(12) United States Patent
Seino et al.

(10) Patent No.: US 7,750,310 B2
(45) Date of Patent: Jul. 6, 2010

(54) SEMICONDUCTOR RADIOACTIVE RAY DETECTOR, RADIOACTIVE RAY DETECTION MODULE, AND NUCLEAR MEDICINE DIAGNOSIS APPARATUS

(75) Inventors: Tomoyuki Seino, Hitachi (JP); Norihito Yanagita, Hitachi (JP); Toshiaki Takai, Yokohama (JP); Chiko Yorita, Fujisawa (JP); Naoki Matsushima, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/501,779

(22) Filed: Aug. 10, 2006

(65) Prior Publication Data

US 2008/0277589 A1    Nov. 13, 2008

(30) Foreign Application Priority Data

Aug. 16, 2005    (JP) ............................. 2005-236017

(51) Int. Cl.
*G01T 1/24* (2006.01)
(52) U.S. Cl. ................................. 250/370.13
(58) Field of Classification Search ............. 250/370.13
See application file for complete search history.

(56) References Cited

U.S. PATENT DOCUMENTS

| 6,236,051 | B1 * | 5/2001 | Yamakawa et al. ....... 250/370.1 |
| 6,777,464 | B1 | 8/2004 | Watanabe et al. |
| 7,247,381 | B1 | 7/2007 | Watanabe et al. |
| 2004/0178426 | A1 * | 9/2004 | Melekhov et al. ........... 257/233 |

FOREIGN PATENT DOCUMENTS

| JP | 58-102532 | 6/1983 |
| JP | 7-50428 | 2/1995 |
| JP | 09-328671 | 12/1997 |
| JP | 10-135436 | 5/1998 |
| JP | 10-163254 | 6/1998 |
| JP | 11/281747 | 10/1999 |
| JP | 11-281747 | 10/1999 |
| JP | 11-304930 | 11/1999 |
| JP | 11-337646 | 12/1999 |
| JP | 2004-128465 | 4/2004 |
| JP | 3587859 | 8/2004 |
| JP | 2005-26419 | 1/2005 |
| JP | 2005-106692 | 4/2005 |
| JP | 2005-257437 | 9/2005 |
| WO | 00/09623 | 2/2000 |

\* cited by examiner

*Primary Examiner*—David P. Porta
*Assistant Examiner*—Marcus H. Taningco
(74) *Attorney, Agent, or Firm*—Mattingly & Malur, P.C.

(57) ABSTRACT

The present invention provides a semiconductor radioactive ray detector having the excellent energy resolution or time precision, a radioactive detection module, and a nuclear medicine diagnosis apparatus. The semiconductor radioactive ray detector has a structure in which plate-like elements made of cadmium telluride and conductive members are alternately laminated and the plate-like element made of cadmium telluride and the conductive member are adhered to each other with a conductive adhesive agent, and the Young's modulus of the conductive adhesive agent is in the range from 350 MPa to 1000 MPa, while the conductive members are made from a material with the linear expansion coefficient of the conductive members in the range from $5 \times 10^{-6}/°C$ to $7 \times 10^{-6}/°C$.

20 Claims, 10 Drawing Sheets

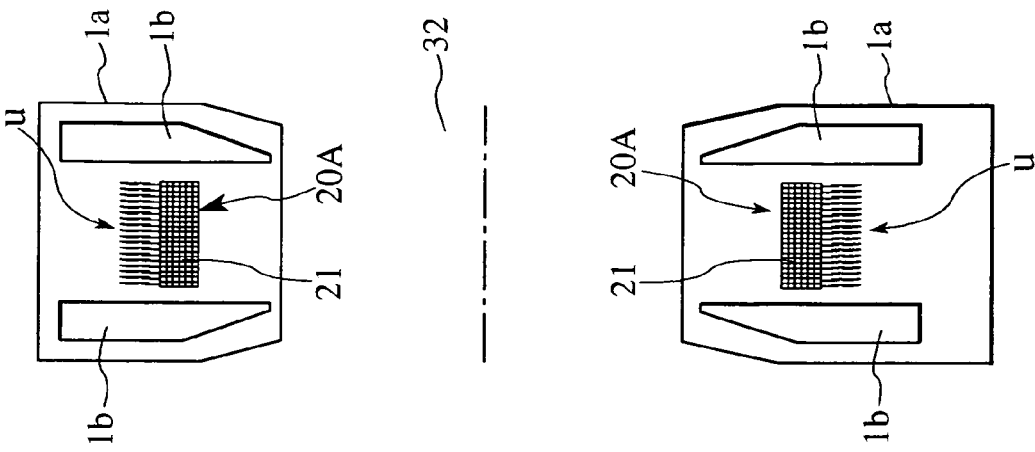
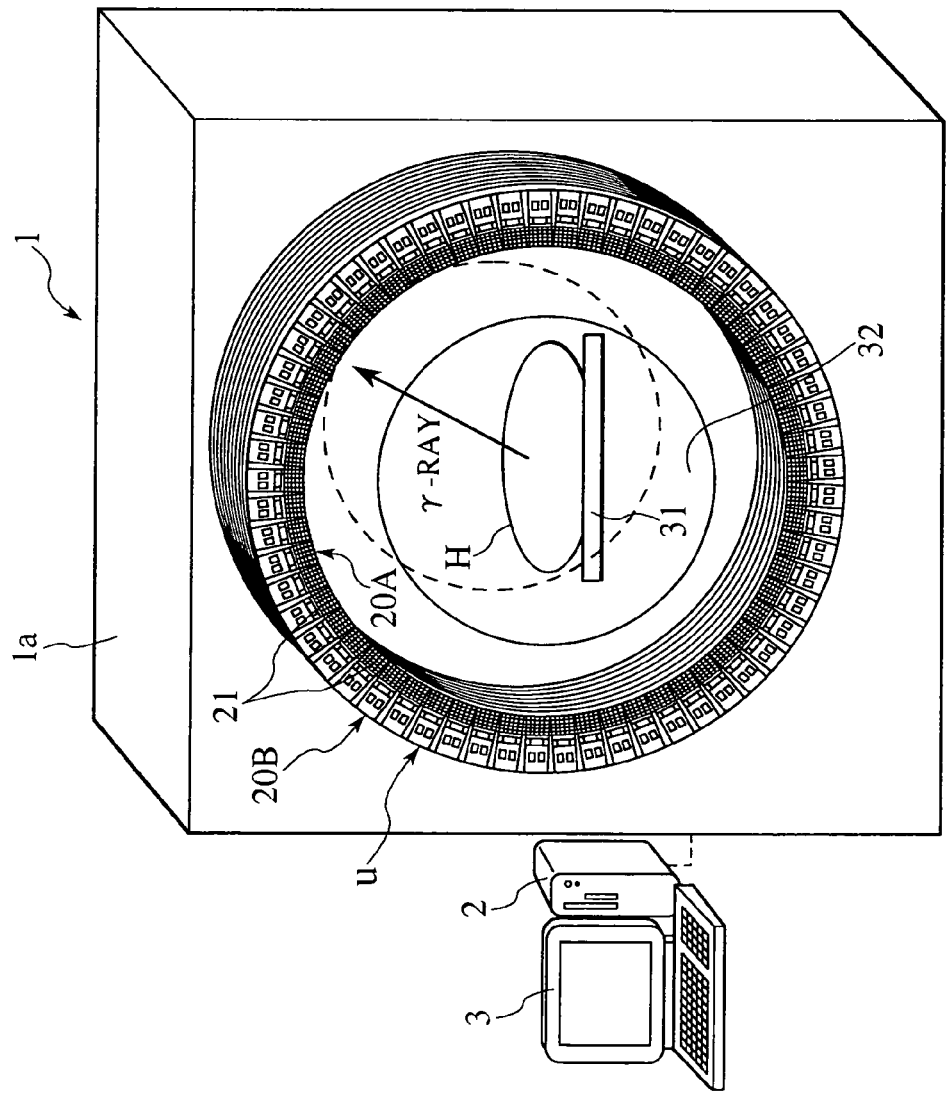

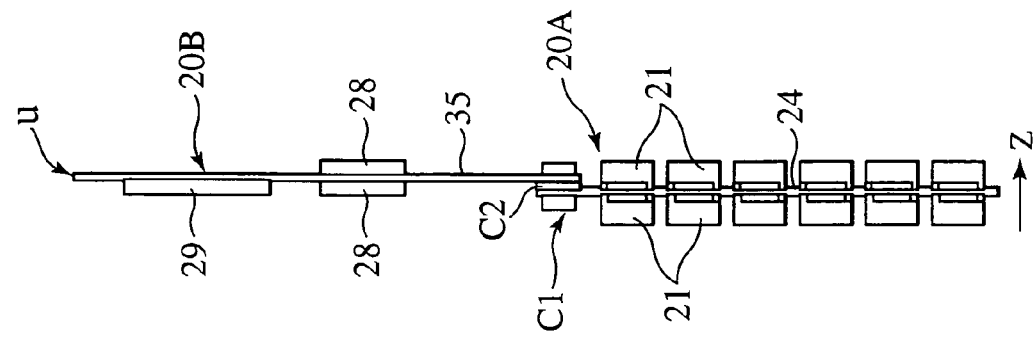
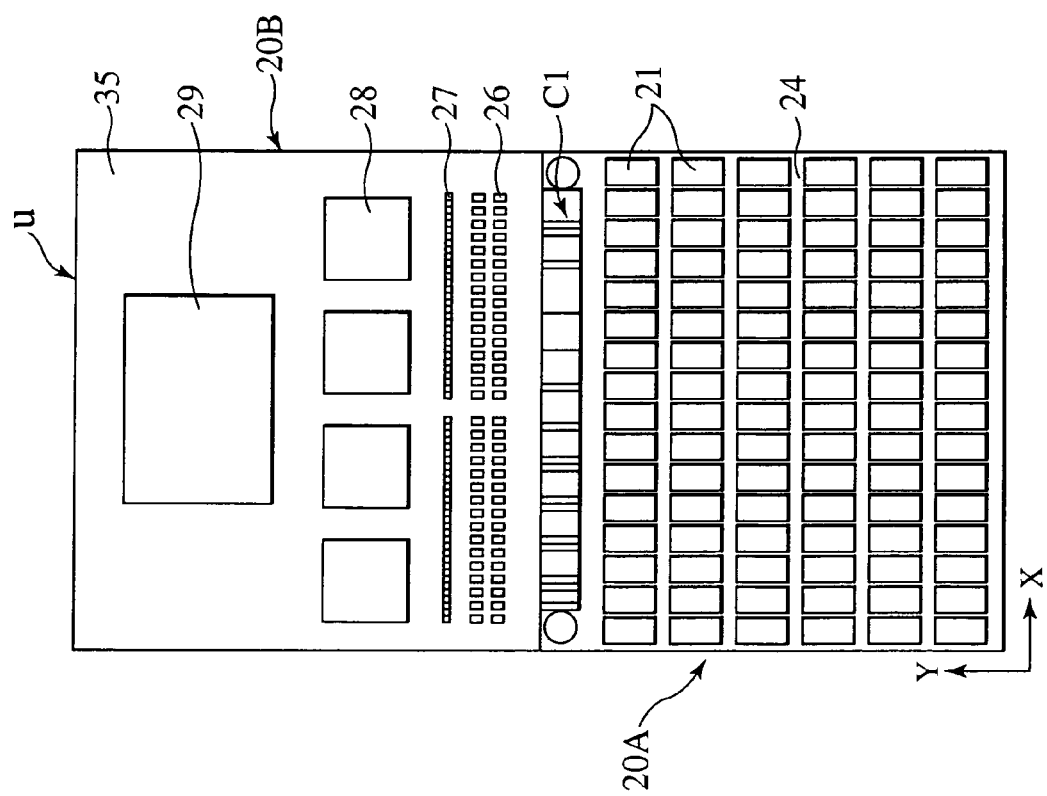

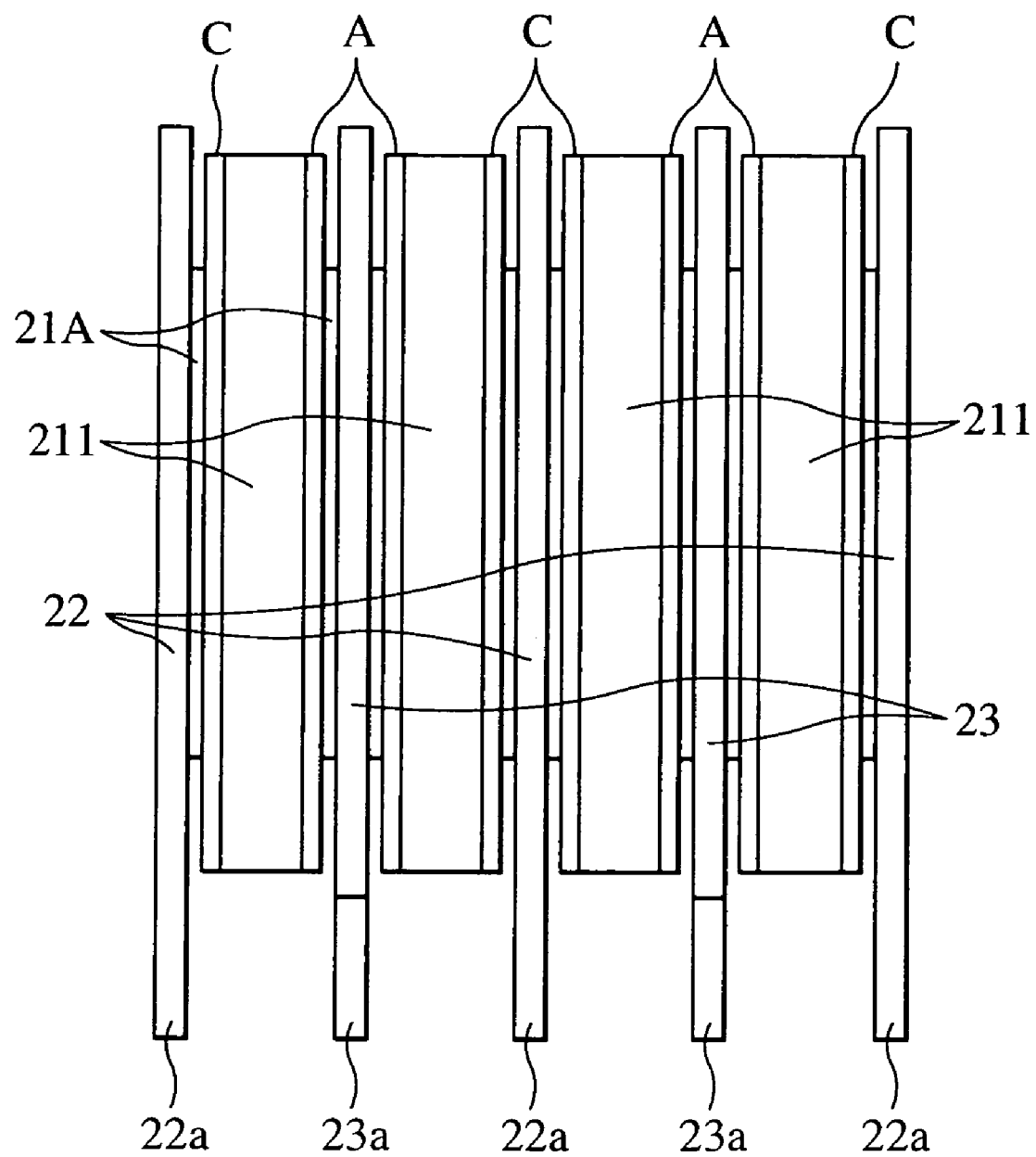

| LONGITUDINAL ELASTIC MODULUS (MPa) \ ENERGY RESOLUTION (%) | MAX | MIN | VARIATION |
|---|---|---|---|
| 50 | 4.7 | 4.5 | 0.2 |
| 350 | 3.0 | 2.9 | 0.1 |
| 500 | 2.5 | 2.4 | 0.1 |
| 1000 | 3.4 | 2.9 | 0.5 |

SEMICONDUCTOR RADIOACTIVE RAY DETECTOR, RADIOACTIVE RAY DETECTION MODULE, AND NUCLEAR MEDICINE DIAGNOSIS APPARATUS

BACKGROUND OF THE INVENTION

The present invention relates to a semiconductor radioactive ray detector having a semiconductor radioactive ray detecting element, a radioactive ray detection module, and a nuclear medicine diagnosis apparatus using the radioactive ray detection module.

Equipment based on the radioactive ray measuring technique has been becoming more and more widespread. In particular, the tendency is remarkable in the field of nuclear medicine, and the representative equipment include positron emission tomographic equipment (PET equipment), single photon emission tomographic equipment (SPECT equipment), and a gamma camera. A radioactive ray detector generally used in the equipment is a combination of a scintillater and a photoelectric multiplier. A scintillater emits light when radioactive rays enter, and the weak light is amplified by the photoelectric multiplier for detection of radioactive rays. Instead of the scintillater, a semiconductor radioactive ray detector using a semiconductor made of a compound such as cadmium telluride (described as CdTe) may be used for measuring radioactive rays. In a semiconductor, when radioactive rays enter, an electric charge, in the form of holes or electrons, is generated because of the photo-electric effect, and the holes or electrons move in an electric field generated by an external voltage applied to the semiconductor. Since the quantity of electric charge is in proportion to the energy of radioactive rays, the energy of the radioactive rays can accurately be detected by accurately measuring the quantity of electric charge.

The CdTe described above has a high effective atomic number as a material for a semiconductor and the sensitivity is high. Furthermore the CdTe has a large band gap of 1.4 V and can work at the room temperature, but also the scintillater has a large atomic number, and there is the need that the sensitivity of CdTe should be made higher to cope with the large atomic number of the scintillater. To satisfy this need, it is conceivable to make a volume of the CdTe portion larger. When a volume of the CdTe portion is made larger, the performance, such as the energy resolution, may disadvantageously decrease. This phenomenon occurs because a carrier life and a carrier mobility of CdTe are not sufficiently long nor large, and also because, when the volume is larger, the carriers easily recombine along the way. When the percentage of recombining and disappearing of carriers is high, a quantity of electric charge cannot accurately be measured. Furthermore, when the volume is larger, a period of time required for movement of carriers becomes longer, so that the electric charge moves for a long time, and the time precision for identifying a point of time when gamma rays enter is deteriorated. This is not advantageous especially for simultaneous measurement of disappearing gamma rays like that performed in the PET equipment. Namely, when the time precision is low, gamma rays cannot be identified discretely, and the direction in which the gamma rays enter cannot be determined disadvantageously.

To overcome the problem described above, it is conceivable to laminate thin crystal of CdTe for use. With this method, because the crystal is thin, a period of time it takes for movement of carriers is short, and the laminated structure allows increase in the volume. The structure can be realized by alternately laminating substrates and crystals as disclosed in Japanese Patent Laid-Open No. 7-50428. Furthermore, when the electrode plates and crystals are alternately laminated as the disclosed in Japanese Patent Laid-Open No. 11-281747, the crystals can be positioned more closer to each other, which enables improvement of the sensitivity.

However, when the electrode plate and CdTe were actually adhered to each other with a conductive adhesive agent and laminated alternately to produce the semiconductor radioactive ray detector, the performance of the semiconductor radioactive ray detector, namely the energy resolution and the time precision thereof were substantially inferior to those of the semiconductor radioactive ray detector without a layered structure. In this case, a number of the semiconductor radioactive ray detectors were not actually used in the measurement.

It was expected that the phenomenon occurs because of deterioration of CdTe caused by a thermal stress. To solve the problem, the conductive adhesive agent was exchanged with a softer conductive agent that more easily followed the thermal stress to produce the semiconductor radioactive ray detector. The thermal stress was sufficiently alleviated, and the number of significantly defective products unusable for measurement was substantially reduced.

However, the energy resolution or the time precision of the semiconductor radioactive ray detector were contrary to the present inventors' expectation and could not reach a sufficiently satisfactory level.

SUMMARY OF THE INVENTION

It is an object of the present invention to provide a semiconductor radioactive ray detector, a radioactive ray detection module, and a nuclear medicine diagnosis apparatus excellent in the energy resolution and the time precision.

The inventors intensively examined the probability of achieving the objects described above and tested various electrode materials and conductive adhesive agents in semiconductor radioactive ray detectors using cadmium telluride as a main material, semiconductor detection modules and nuclear medicine diagnosis apparatuses. As a result, the inventors found that the semiconductor radioactive ray detector having the characteristics comparable to those of semiconductor radioactive ray detectors without laminated crystals is obtained, and have arrived at the present invention.

Specifically, according to an aspect of the present invention, there is provided a semiconductor radioactive ray detector using cadmium telluride as a main material and having a structure with plate-like elements made of cadmium telluride and metallic conductive members laminated alternately, said plate-like element made from cadmium telluride and said metallic conductive element being adhered to each other with a conductive adhesive agent, wherein said conductive adhesive agent has the Young's modulus (the longitudinal elastic modulus) in the range from 350 MPa to 1000 MPa and said metallic conductive member is made from a material having the linear expansion coefficient in the range from $5\times10^{-6}/^\circ$ C. to $7\times10^{-6}/^\circ$ C.

In the semiconductor radioactive ray detector according to the present invention, unlike the conventional technology, a conductive adhesive agent, which is a rigid conductive adhesive noncompliant to thermal stress (with a Young's modulus from 350 MPa to 1000 MPa), is used to improve electric conductivity of a metallic filler contained in the conductive adhesive agent and also to avoid distortion of a signal passing therethrough. Furthermore, in the semiconductor radioactive ray detector according to the present invention, the metallic members whose linear expansion coefficient is close to that of the plate-like element of cadmium telluride as a main material of the semiconductor radioactive ray detector, namely in the range from $5 \times 10^{-6}/°$ C. to $7 \times 10^{-6}/°$ C., is used, so that the possibility of generation of thermal stress in the plate-like element of cadmium telluride and the electrode plate can be minimized. Because of these features, it is possible to obtain a semiconductor radioactive ray detector with the improved gamma ray detection sensibility and also with the elevated higher energy resolution and time precision.

Further, a nuclear medicine diagnosis apparatus includes the semiconductor radioactive ray detector having the configuration described above, a radioactive ray detection module with a wiring board with the semiconductor radioactive ray detector attached thereon, and an image information forming device for forming an image using information acquired based on a radioactive detection signal outputted from the semiconductor radioactive ray detector. With the configuration described above, it is possible to obtain a nuclear medicine diagnosis apparatus excellent in the energy resolution and time precision and enabling acquisition of high precision images. Furthermore, with the present invention, it is possible to shorten the time required for examination and reduce a radioactive medical agent administered to a subject, which in turn allows reduction of an exposure rate of the subject subjected to radiation.

The present invention makes it possible to obtain a semiconductor radioactive ray detector excellent in the energy resolution and the time precision, a radioactive ray detection module, and a nuclear medicine diagnosis apparatus.

These and other objects, features and advantages of the present invention will become more apparent in view of the detailed description of the preferred embodiments in conjunction with the drawings.

BRIEF DESCRIPTION OF THE DRAWINGS

FIG. 1A is a perspective view schematically showing a configuration of PET equipment according to a first preferred embodiment of the present invention;

FIG. 1B is a cross-sectional view illustrating the PET equipment shown in FIG. 1A taken along the longitudinal direction;

FIG. 2A is a front view illustrating a unit substrate used in the PET equipment shown in FIG. 1;

FIG. 2B is a side view illustrating the unit substrate shown in FIG. 2A;

FIG. 4 is an enlarged view illustrating the detector viewed in the incoming direction of gamma rays;

DESCRIPTION OF THE PREFERRED EMBODIMENTS

Figure 3A:
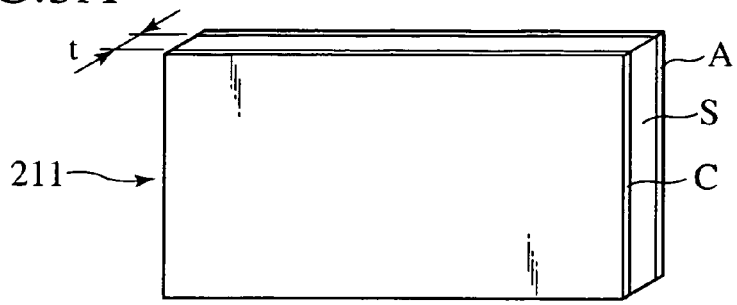
FIG. 3A is a schematic perspective view illustrating a semiconductor radioactive ray detecting element.
Figure 3B:
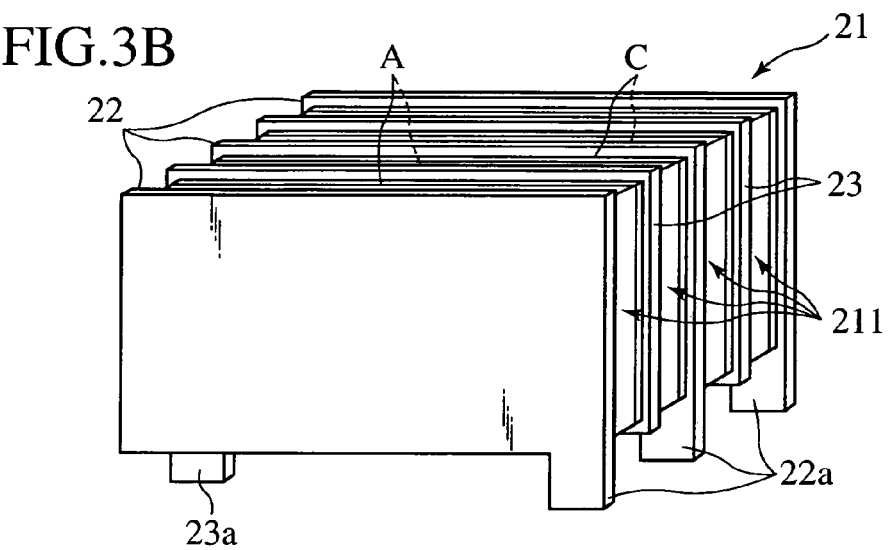
FIG. 3B is a perspective view illustrating a semiconductor radioactive ray detector using the element therein.

PET equipment according to a preferred embodiment of the present invention will be described in detail with reference to the drawings as a nuclear medicine diagnosis apparatus using a semiconductor radioactive ray detector according to the present invention.

Embodiment 1

The PET equipment according to the present embodiment includes, as shown in FIG. 1A, PET equipment 1, a bed 31 for supporting a subject (a person to be examined) H, a data processor (a computer or the like) 2, and a display unit 3. The PET equipment 1 has a number of unit substrates U positioned in the circumferential direction as shown in FIGS. 2A and 2B. In the PET equipment 1, the subject H is laid on the bed 31 movable in the longitudinal direction, and moved into a column-shaped measuring space 32 surrounded by the unit substrates U.

[PET Equipment]

The PET equipment 1 includes a number of unit substrates U positioned in the circumferential direction surrounding the measuring space 32 in which the bed 31 is moved. A plurality of the unit substrates U are positioned in the longitudinal direction of the bed 31 (the axial direction of the measuring space 32). The unit substrate U includes, as shown in FIGS. 2A and 2B, a radioactive ray detection module (hereinafter referred to as "a detection module") 20A and an application-specific integrated circuit substrate (hereinafter referred to as "an ASIC substrate") 20B. The detection module 20A includes a plurality of semiconductor radioactive ray detectors (hereinafter referred to just as "detectors") 21. The detectors 21 detect gamma rays emitted from a body of the subject H. A detailed description of the detectors 21 is provided below.

The ASIC substrate 20B includes integrated circuits (analogue ASICs 28 and a digital ASIC 29) for measuring pulse-height values of detected gamma rays and points of time when gamma rays are detected, and measures pulse-height values of detected radioactive rays (gamma rays) and points of time when radioactive rays are detected. The integrated circuits include a plurality of signal processors for processing signals indicating detections of radioactive rays.

A detailed description of the PET equipment 1 is provided below.

[Semiconductor Radioactive Ray Detector]

Figure 3C:
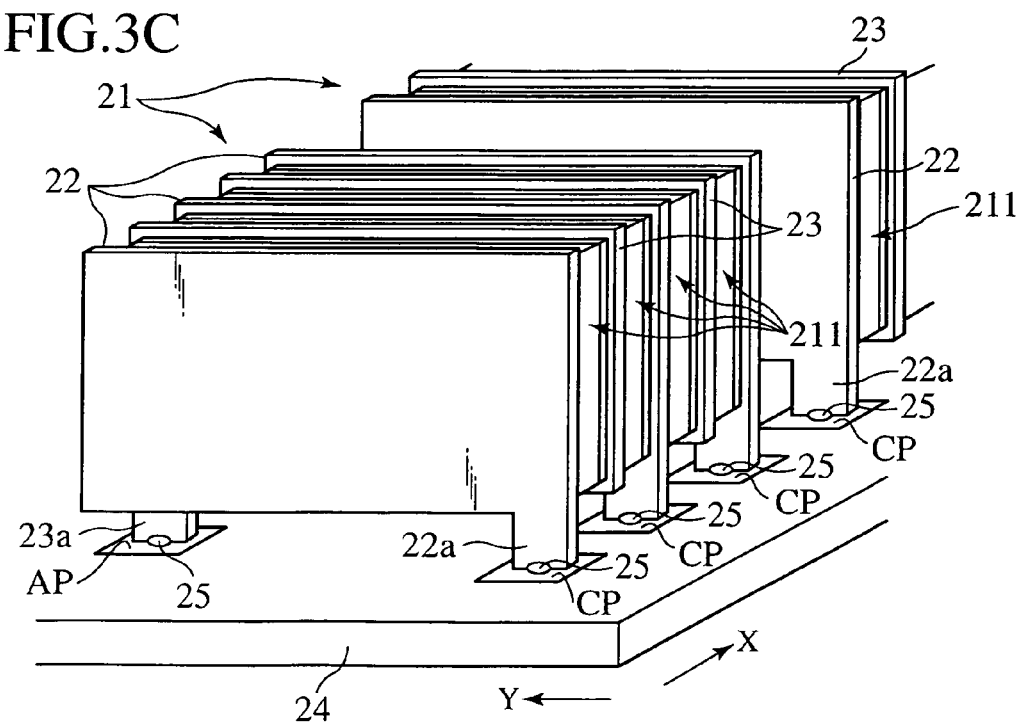
FIG. 3C is a view schematically showing the state in which the detector is provided on a wiring board.

The detector 21 according to the present embodiment is described below. As shown in FIG. 3C, the detector 21 includes four semiconductor radioactive ray detecting elements (hereinafter referred to as "detecting elements", see FIG. 3C) 211 and conductive members 22, 23 positioned between the detecting elements 211 and on the both ends of the detector 211. The detecting element 211 includes, as shown in FIG. 3A, a semiconductor element S (a plate-like element) comprising a plate-like semiconductor material, and thin film-like electrodes are formed on both side faces of the semiconductor element S by the deposition method or the like. An electrode formed on one side face is an anode electrode (hereinafter referred to as "an anode") A, and another electrode formed on the other side face is a cathode electrode (hereinafter referred to as "a cathode") C. The detector 21 has a configuration in which an even number of the detecting elements 211 (four numbers of the detecting elements 211 in the present embodiment) each with the anode A and the cathode C longitudinally positioned perpendicular to a mounting surface of the wiring board 24 (see FIG. 2) are positioned in parallel with the direction (direction X in FIG. 3C) perpendicular to the incoming direction of a radioactive ray (direction Y in FIG. 3C) so that the anodes A and the cathodes C face each other, and same types of electrodes (the anodes A and the cathodes C) are electrically connected each other via the conductive members 22, 23. Namely, the conductive members 23 are, as shown in FIG. 4, positioned between the anodes A facing each other adjacent to the detecting elements 211, and are attached to each anode A with an electrically conductive adhesive agent 21A. The conductive member 22 is positioned between the cathodes C facing each other adjacent to the detecting elements 211, and attached to each cathode C with the electrically conductive adhesive agent 21A. Furthermore, the conductive members 22 are attached to each cathodes C positioned on the both ends of the detector 21 in the direction X (see FIG. 3C). In the detector 21, the anodes A and the cathodes C are positioned alternately, and also the conductive members 22, 23 are positioned alternately.

The semiconductor element S is an area for generating an electric charge by reacting with radioactive rays, and is made of a single crystal of CdTe, CdZnTe, GaAs, and the like. The cathode C and the anode A are made of any one of Pt, Au, In, and the like as a material. According to the present embodiment, the detecting element 211 forms a pn junction diode, for instance, by using CdTe as the semiconductor element S, the Pt-based cathode C, and the In-based anode A.

Descriptions are provided below for a relation between the time and the pulse-height value curve in the case where the thickness t of the semiconductor element S (see FIG. 3A) is thick and in the case where the thickness t of the semiconductor element S is thin. When the same level of a reverse bias voltage (hereinafter referred to as "a bias voltage") on the pn junction is applied to a section between the cathode C and the anode A, in the case where the thickness t of the semiconductor element S is thin, the elevation (rising edge) of a pulse-height value is fast, and the precision of a pulse-height value (energy resolution) is high. When the rising rate of the pulse-height value is fast, for instance, the precision of simultaneous measurement (the simultaneous measurement resolution) in the PET equipment 1 is improved. As the rate of rise is faster, the energy resolution, in the case that the thickness t of the semiconductor element S is thin, becomes higher (the collection efficiency of electric charge is getting increased), because a period of time until an electron reaches the anode A and a period of time until a positive hole reaches the cathode C are both reduced. In other words, the time required for collection of an electric charge is reduced. Furthermore, in the case that the thickness t is thin, the positive hole, otherwise disappearing before reaching, may reach the cathode C without disappearing. The thickness t may be interpreted as an inter-electrode distance between the cathode C and the anode A. The anode A is an electrode for extracting signals indicating detections of radioactive rays, and the cathode C is an electrode for applying a bias voltage.

The thickness (inter-electrode distance) t of the semiconductor element S is preferably in the range from 0.2 millimeter to 2 millimeters. When the thickness t is more than 2 millimeters, not only the rising rate of a pulse-height value becomes slower, but also the highest pulse-height value becomes lower. Even if the thickness t is thick, the migration rate of electrons and positive holes can be improved by raising the bias voltage and the electric field intensity in the depth direction of the detecting element 211, so that a period of time until electrons and electron holes reach relevant electrodes may be reduced. However, increase of the applied bias voltage may disadvantageously cause negative effects such as a larger-sized direct current high voltage power supply and an insulation breakdown inside the wiring board 24 or the like. When the thickness t is less than 0.2 millimeter, the thickness (volume) of the electrodes (the cathode C and the anode A) relatively increases. In this case, a proportion of the semiconductor elements S reacting with radioactive rays, decreases. Namely, when the thickness t of the semiconductor element S is small, electrodes (the anode A and the cathode C) that do not react with gamma rays, more specifically that do not detect gamma rays, relatively increases in thickness, and at the same time, a proportion of the semiconductor elements S that react with gamma rays relatively decreases, and therefore the sensitivity for detecting gamma rays becomes lower. Furthermore, when the thickness t is small, the electrostatic capacitance in each detecting element 211 increases. The electrostatic capacitance is equal to the input capacitance when viewed from the side of the signal processing circuit (the ASIC), so that, as the input capacitance is larger, noises in the signal processing circuit occurs easily, and the energy resolution and the simultaneous counting resolution are easily degraded. Furthermore, volumes of the detectors 21 are effectively assured by positioning the detecting elements 211 in parallel to assure the appropriate detection sensitivity in each detector 21, so that, as the thickness t is thinner, the number of elements positioned in parallel has to be increased more. As a result, the electric capacitance in each detector synergistically increases, and there may be caused the performance degradation (such as degradation in the contrast of PET images due to a degradation in the energy resolution, an increase of the inspection time and a degradation in the image quality due to a degradation in the simultaneous counting resolution, or the like) in the PET equipment 1. Therefore, the thickness t is preferably in the range from 0.2 millimeter to 2 millimeters as described above.

The conductive members 22, 23 each have a plate-like shape and are made from a material with the linear expansion coefficient in the range from $5 \times 10^{-6}/°C$ to $7 \times 10^{-6}/°C$. The material is selected from the group consisting of iron-nickel alloy, iron-nickel-cobalt alloy, chromium, and tantalum. In this embodiment, the 42% alloy (Fe 58% and Ni 42%) may be used as an iron-nickel alloy; and the kovar (Fe 54%, Ni 29%, and Co 17%) may be used as an iron-nickel-cobalt alloy. CdTe, a main material of the detecting element 211, has the linear expansion coefficient of $6\pm0.1\times10^{6}/°$ C. Namely, the material with a linear expansion coefficient close to that of CdTe is used for the conductive elements 22, 23. As a result, the thermal stress can be kept at a sufficiently low level due to the interactive effect with the conductive adhesive agent 21A described bellow.

In this embodiment, the conductive members 22, 23 are formed to cover each electrode surface of the detecting element 211 and the members are larger than any of the electrode surfaces. The size of the electrode members 22, 23 may be equal to that of the detecting element 211. The thickness of the conductive members 22, 23 is approximately in the range from 10 micrometers to 100 micrometers, preferably approximately 50 micrometers. In the state where the conductive members 22, 23 are attached to the detecting element 211, the protruding sections 22a, 23a provided on the conductive members to extend downward (the wiring board 24 side) from the semi-conductor element S. In the embodiment, the conductive members 22, 23 are positioned between the detecting elements 211 or at two ends of the detector 21 and attached in the alternative direction such that the protruding sections 22a, 23a protrude at different positions in a lower face (the surface facing the wiring board 24) of the semi-conductor element S. Specifically, the conductive members 22, 23 are attached so that the protruding sections 22a are positioned at a front side and the protruding sections 23a are at a rear side in a direction of the semi-conductor element S in which the radioactive ray goes (indicated by Arrow Y in FIG. 3C. Because of this configuration, the detector 21 has three protruding sections 22a at the front side thereof and two protruding sections 23a at the rear side thereof. The protruding sections 22a, 23a work, as shown in FIG. 3C, as securing sections for securing the detector 21 to the wiring board 24. The protruding sections 22a are connected to the connecting member CP for cathode C provided on the wiring board 24, and the protruding sections 23a are connected to the connecting member AP for anode A provided on the wiring board 24. The detector 21 is adhered on the wiring board 24 in a non-contact manner with the protruding sections 22a, 23a. Namely, gaps are provided between the wiring board 24 and the detecting element 211. The gaps advantageously prevent decrease in the insulation property caused by dust clogging up between the detector 21 and the wiring board 24. In addition, the detector 21 can be cooled down using the high ventilation property caused by the gaps. A bottom of the detector 21 may be coated with an insulating material (not shown) to prevent unexpected insulation breakdown.

The protruding sections 22a, 23a are required only to have a size enough to make the detector 21 stably attach to the wiring board 24. The protruding sections are preferably formed to be thin as much as possible in the Y axial direction shown in FIG. 3C. Because of this configuration, the protruding sections 22a, 23a can reduce the scattering ratio of gamma rays and also can reduce the heat emitted from the wiring board 24 transferring to the detector 21 through the protruding sections 22a, 23a, which helps to keep the properties of the detector 21 stable.

The conductive members 22, 23 are adhered and attached to the detecting element 211 with the conductive adhesive agent 21A. A material prepared, for instance, by dispersing conductive particles like metallic powders in an insulative adhesive agent made from an organic polymer material is used as the adhesive agent 21A. The material should be hard one with the Young's modulus (the longitudinal elastic modulus) in the range of 350 to 1000 MPa, preferably 500 MPa.

When the directing element 211 is adhered to the conductive members 22, 23 with the conductive adhesive agent 21A, a heating process at a high temperature in the range from 120 to 150° C. is necessary for hardening the conductive adhesive agent 21A. In the case where there is a gap between the detecting element 211 and the conductive members 22, 23 in thermal expansion (i.e., the linear expansion coefficient), remarkable distortion occurs to the thermal stress. To solve the problems caused by the thermal stress, a soft conductive adhesive agent is generally used. However, when the soft conductive adhesive agent is used, energy resolution and time accuracy of the detector cannot be achieved with the sufficient level as a detector. This is because the soft adhesive agent does not have enough adhesive property to contact metallic fillers contented therein and contact failure will occur. When the detecting signal outputted from the detecting element 211 goes through a position where contact failure is occurring, the signal is deformed because the signal is a high frequency wave with the frequency of above 10 MHz. As a result, deterioration of performance such as, increase of noises occurs. Therefore, the soft conductive adhesive agent is not suitable for adhering the detecting element 211 and the conductive elements 22, 23.

On the other hand, because the conductive agent 21A according to the embodiment is made of a hard material with the Young's modulus in the range from 350 to 1000 MPa, the metallic filler contained therein can be contacted sufficiently and preferable conductive state can be obtained after hardening. As a result, the problems caused by the soft conductive adhesive agent described above can be solved. However, the hard conductive adhesive agent 21A may disadvantageously increase the thermal stress caused by the gap between the detecting element 211 and the conductive members 22, 23 in thermal expansion (i.e. the linear expansion coefficient). To overcome the disadvantage, the embodiment, a material for the conductive members 22, 23 with the linear expansion coefficient in the range of $5\times10^{-6}/°$ C. to $7\times10^{-6}/°$ C. close to $6\times10^{-6}/°$ C. that of CdTe is used, which enables the thermal stress to be kept at the allowable low level.

The thermal stress added to the detecting element 211 remarkably affects the properties of the detector 21 such as energy resolution and time accuracy, and then causes deterioration of the detector 21. Therefore, keeping the thermal stress at the sufficient low level is helpful for improving the properties of the detector 21. In the embodiment, since the thermal stress can be kept at the allowable level, the properties little deteriorate even when the detector is formed by laminating the detecting element 211 and the conductive members 22, 23. Also, because the thermal stress is suppressed to a sufficiently low level, the detecting element 211 can be thinner for enabling lamination. Therefore, the detector 21 realizes increasing both the property performances and sensitivity at one time.

The conductive members 22, 23 made from the iron-nickel allow (the 42% alloy (Fe 58%, Ni 42%)) were adhered to the detecting element 211 with the conductive adhesive agent 21A having the having the Young's modulus 500±50 MPa, and a test was performed for measuring the energy spectrum of 137 Cs (a material emitting gamma rays of 662 keV). Then no defective product was produced and the energy resolution of 2.5% was obtained. In addition, when the similar measuring test was performed before adhering the detecting element 211 and the conductive members 22 23 to each other, the energy resolution was 2.2%. Accordingly, taking into account that increase of electrical capacitance caused by laminating the detecting element 211 brings about increase of noise, it is concluded that the properties scarcely deteriorate. When the iron-nickel-cobalt alloy (the kovar (Fe 54%, Ni 29%, and Co 17%)) or the tantalum was used as the conductive members 22, 23 and the test was performed, the energy resolution marked at 2.5% equal to that of the iron-nickel alloy, and when the chromium was used, the energy resolution marked at 3%.

As a comparative example, semi-conductor detectors were produced using the conductive members 22, 23 made from the conventional copper base alloy and the conductive adhesive agent with the Young's modulus of 500 MPa. When the similar test was performed, a half of the products were defective because of too much noise and the remaining half had poor properties marking at above 4% of the energy resolution. Next, the semiconductors were produced using the conductive members 22, 23 made from the copper base alloy and the conductive adhesive agent having the Young's modulus of elasticity of 50 MPa. When the similar test was performed, a percentage of the defective product decreased to approximately 10%, but the product had the energy resolution as low as 4%, which was below the desirable level.

Figure 5:
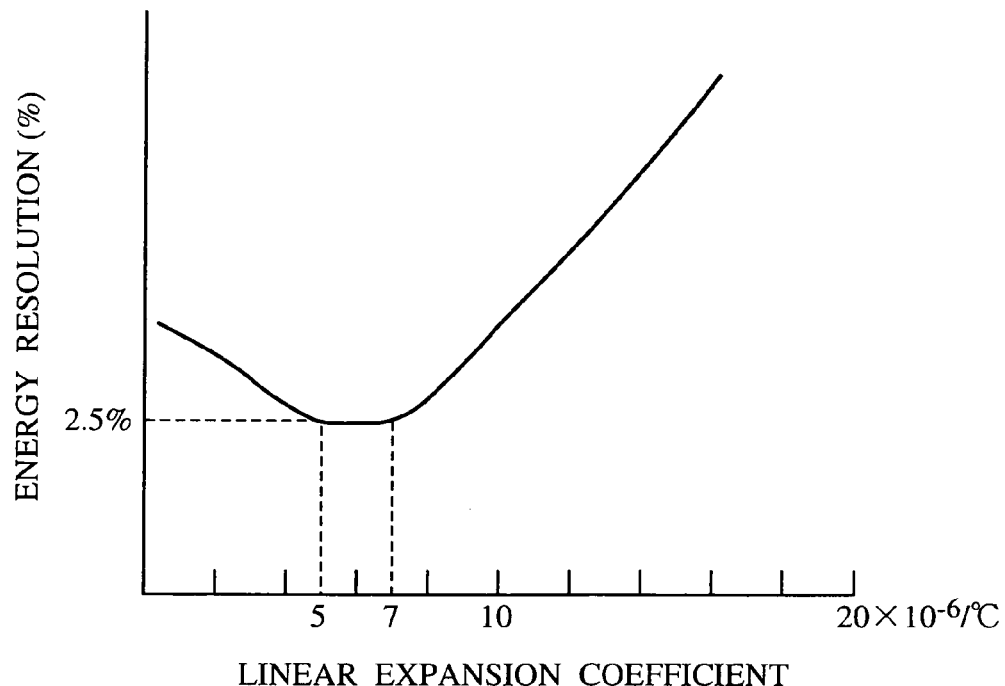
FIG. 5 is a graph showing a relation between the energy resolution and a linear expansion coefficient of a conductive member when a linear expansion coefficient of a conductive adhesive agent is 500 MPa.
Figure 6:
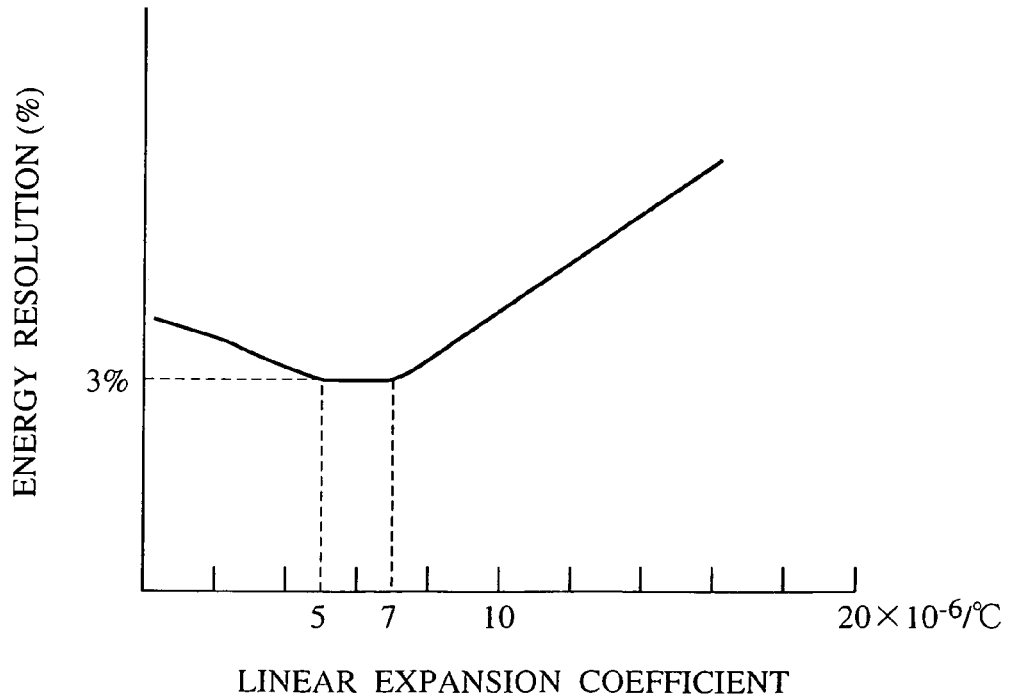
FIG. 6 is a graph showing a relation between the energy resolution and a linear expansion coefficient of a conductive member when a linear expansion coefficient of a conductive adhesive agent is 350 MPa.

FIG. 5 is a graph illustrating the relation between the energy resolution and the linear expansion coefficient of the conductive members 22, 23 in the state where the Young's modulus of elasticity of the conductive adhesive agent 21A is 500 MPa; and FIG. 6 is a graph illustrating the relation between the energy resolution and the linear expansion coefficient of the conductive members 22, 23 in the state where the Young's modulus the conductive adhesive agent 21A is 350 MPa. In both of the figures, the vertical axis indicates an energy resolution, and the horizontal axis indicates a linear expansion coefficient.

As shown in FIG. 5, when the conductive members 22, 23 has the linear expansion coefficient in the range from $5 \times 10^{-6}/°$ C. to $7 \times 10^{-6}/°$ C., the energy resolution marked at 2.5%, indicating that the product is at the desirable property level.

As shown in FIG. 6, when the Young's modulus of elasticity of the conductive adhesive agent 21A is 350 MPa and when the conductive members 22, 23 has the linear expansion coefficient in the range from $5 \times 10^{-6}/°$ C. to $7 \times 10^{-6}/°$ C., the energy resolution marked at 3.0%, indicating that the product is slightly below the certain level but obtains the desirable properties. The angle of the line segment shown in FIG. 6 becomes slightly flat, which shows that the degree of dependence on the linear expansion coefficient of the conductive members 22, 23 becomes low.

Figure 7:
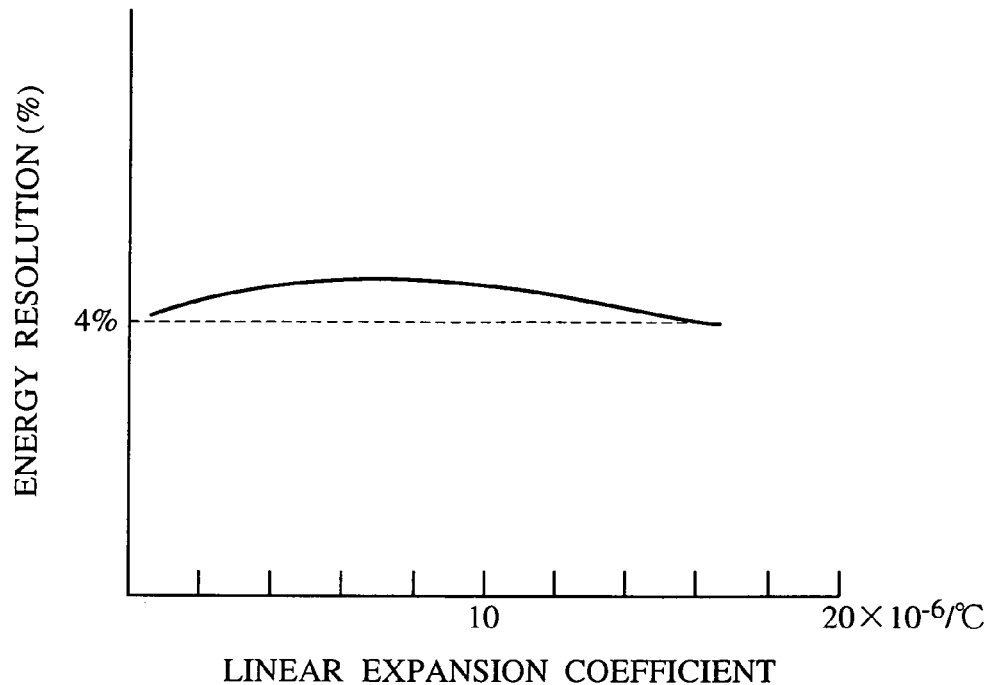
FIG. 7 is a graph showing a relation between the energy resolution and a linear expansion coefficient of a conductive member when a linear expansion coefficient of a conductive adhesive agent is 50 MPa.
Figure 8:
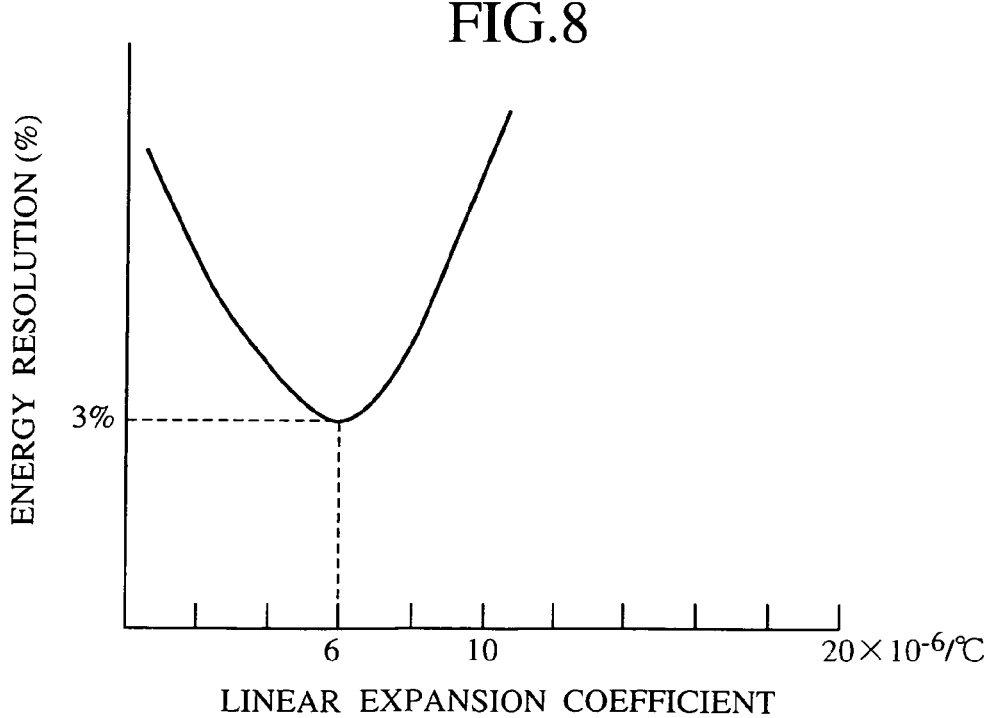
FIG. 8 is a graph showing a relation between the energy resolution and a linear expansion coefficient of a conductive member when a linear expansion coefficient of a conductive adhesive agent is over 1000 MPa.

FIG. 7 is a graph showing a comparative example in which the Young's modulus is 50 MPa. Namely, in this comparative example, the Young's modulus of the conductive adhesive agent 21A is not in the range from 350 MPa to 1000 MPa. FIG. 8 is a graph also showing a comparative example in which the Young's modulus is more than 1000 MPa (1200 MPa).

As shown in FIG. 7, the dependence on the linear expansion coefficient becomes smaller, but the energy resolution becomes larger at any linear expansion coefficient with the dispersion increasing.

Furthermore, as shown in FIG. 8, when a conductive adhesive agent having the Young's modulus of more than 1000 MPa (1200 MPa) is used, performance of the conductive members 22, 23 rapidly changes according to the linear expansion coefficient, and a minim value of the energy resolution is 3%. From this fact, it can be understood that, when a conductive adhesive agent having the Young's modulus of more than 1000 MPa is used, even if a different between a linear expansion coefficient of the detecting element 211 and that of the conductive members 22, 23 is small, the thermal stress becomes larger with the energy resolution deteriorated.

Therefore, it is understood that it is preferable to use the conductive adhesive agent 21A with the Young's modulus in the range from 350 MPa to 1000 MPa. The hardness, namely Young's modulus of the conductive adhesive agent 21A used in the present invention is based on a value obtained through measurement with a tensile elasticity measuring device. The linear expansion coefficients of the conductive members 22, 23 are based on values obtained through measurement with a TMA (thermo mechanical analysis) device.

In this embodiment, each of the semiconductors S provided in parallel to each other has the thickness t (in the range from 0.2 to 2 mm) described above. The thickness of the cathode C and the anode A is at most several micrometers. In the detector 21, the cathodes C in a plurality of detecting elements 211 are connected in common and also the anodes A in the detecting elements are connected in common, so that it is not possible to identify in which detecting element the semiconductor element S reacts with the gamma rays. The configuration of the detector 21 is employed for making smaller the thickness t of the semiconductor element S (Refer to FIG. 3A) to improve the efficiency in collection of an electric charge, for raising an uprising speed of a pulse-height value to improve the energy resolution, and also for reducing a quantity of gamma rays passing through the parallel arrangement of the semiconductor elements S so that the semiconductor S reacts with the gamma rays more (for raising a count value of the gamma rays). Increase of the count number of gamma rays leads to improvement of sensitivity of the detector 21.

Outline of a principle in detection of gamma rays by the detector 21 is described below. When the gamma rays comes in along the direction Y into the detector 21 and reacts with the semiconductor S, pairs of a hole and an electron are generated in proportion to a quantity of the energy of the gamma rays. However, the bias voltage for electric charge collection from a DC high voltage power (not shown) (for instance −500 V to the cathode C and a voltage close to the ground potential to the anode A, namely a reverse-directional voltage set so that an electric potential at the anode A is higher by 500 V as compared to that at the cathode C) is applied to a section between the cathode C and the anode A in the detecting element 211 constituting the detector 21. Because of this feature, a positive hole equivalent to a positive electric charge is drawn and moves toward the cathode C, while an electron as a negative electric charge is drawn and modes toward the anode A. When the positive hole is compared with an electron, since the mobility of the electron is relatively higher than that of the positive hole, the electron reaches the anode A within a relatively shorter period of time. On the other hand, since the mobility of the positive hole is relatively low, the positive hole reaches the cathode C spending a relatively longer period of time. It is to be noted that electrons and positive holes may sometimes be trapped on the way before reaching the electrodes.

The conductive member 23 provided between the anodes A and the conductive member 22 provided between the cathodes C are insensitive regions where the gamma rays are not detected. Therefore, in the detector 21, the conductive members 23, 22 are provided between the detecting elements 211, more specifically between the electrodes. It is to be noted that also the anode A and the cathode C are insensitive regions.

The detectors 21 are provided, as shown in FIG. 2A and FIG. 2B, for 6 channels on the wiring board 24 of the detection module 20A along the direction Y from the detection module 20A to the ASIC substrate 20B (in the radial direction of the PET equipment), for 16 channels in the direction X (circumferential direction of the PET equipment 1) perpendicular to the direction Y, and also for 2 channels (on both surfaces of the wiring board 24) along the thickness direction of the wiring board 24 (toward the depth of the PET equipment). With the configuration as described above, the detectors 21 are provided for 96 channels on one surface of the wiring board 24, and for 192 channels in all on both surfaces of the wiring board 24.

Although the detectors 21 are provided on both surfaces of the wiring board 24 in this embodiment, the configuration is allowable in which the detectors are provided only on one surface thereof. Furthermore, the detector 21 is preferably coated with an insulating material to prevent dielectric breakdown. Coat of the insulating material can be formed with the thickness of several tens microns by immersing the detection module 20A as a whole in an insulating material such as silicone rubber and then drying the insulating material.

[Unit Substrate]

Detailed structure of the unit substrate U is described below with reference to FIGS. 2A and 2B. The unit substrate U consists of a detection module 20A with a plurality of detectors 21 provided thereon as described above and an ASIC substrate 20B. The ASIC substrate 20B includes condensers 26, resistors 27, analog ASIC 28, and a digital ASIC 29.

[Detection Module]

As illustrated in FIG. 4, there are a plurality of detection units 21 provided on the wiring board 24 to constitute a detection module 20A. A voltage, such as 500 Volt, is applied between the anode A and the cathode C of each detection units 21 to collect electric charges emitted therein as described above. The voltage applied between the anode A and cathode C of each detection unit 21 is provided from a power wire line (not shown) on the ASIC substrate 20B, through the connector C1 and a power line (not shown) provided on the wiring board 24 of the detection module 20A. The detection module 20A has the connector C1 at the end of the wiring board 24 on the ASIC substrate side. The connector C1 has the terminal 33 and a plurality of terminals 34 as described above. The gamma rays detection signal outputted from each detection unit 21 is transmitted to the ASIC substrate 20B through the connector C1.

[ASIC Substrate]

As illustrated in FIGS. 2A and 2B, four analog ASICs 28 and one digital ASIC 29 are arranged on the one surface of the wiring board 35 of the ASIC substrate 20B. Furthermore, as illustrated in FIG. 2B, additional four analog ASICs 28 are also arranged on the other surface of the wiring board 35. Therefore, one ASIC substrate 20B has a total of eight analog ASICs arranged thereon. On both surfaces of the wiring board 35 are also arranged an appropriate number of both condensers 26 and resistors 27 based on the number of the detector unit 21 arranged thereon. In addition, there are a plurality of wire lines (not shown) in the wiring board 35 to provide electrical connections between the condensers 26, the resistors 27, the analog ASICs 28, and the digital ASIC 29. These wire lines constitute a laminated wiring structure in the wiring board 35. The condensers 26, the analog ASICs 28, and the digital ASIC 29 arranged thereon are advantageously arranged in the order of how the signals sequentially pass through from the detection units 21 of the protection module 20A. One end of the resistor 27 is connected to the input side of the condenser 26, and the other end of the resistor 27 is connected to a ground line (not shown) provided in the wiring board 35. The analog ASIC 28, a kind of LSI, as described herein refers to an ASIC (Application Specific Integrated Circuit) adapted to a specific application that processes an analog signal (a gamma rays detection signal) outputted from the detection unit 21. The analog ASIC 28 has a plurality of signal processing circuits provided therein, each circuit responding to each detection unit 21 connected thereto. These signal processing circuits are designed to receive the gamma rays detection signal (radio active detection signal) outputted from the corresponding one detection unit 21 and then to measure the peak value of the gamma rays detection signal.

A connector C2 is provided at the end on the detection module side of the wiring board 35 of the ASIC substrate 20B, the connector C2 having a plurality of connectors (e.g. spring pin connector), each of which is connected to each corresponding condenser 26.

The unit substrates U are arranged on a ring-like supporting members (not shown) arranged in the PET equipment 1 so that the surface, where detection units 21 are mounted thereon, of the unit substrate should face the depth direction of the PET equipment 1 (i.e. the longitudinal direction of the bed 31, and also the direction z showed in FIG. 2B). The ring-like supporting members are arranged so that the members surround the periphery of the measuring region 32. A plurality of unit substrates U arranged on the ring-like members are also arranged in the circumferential direction so that the substrates surround the periphery of the measuring region 32. Also, the detection modules 20A are allocated on the inner side (on the measurement region 32 side), and, on the other hand, the ASIC substrates 20B are allocated on the outer side. In this embodiment, additional unit substrates U are arranged further behind in the depth direction of the PET equipment 1. In the unit substrates U as described above, the direction x illustrated in Figures, such as FIG. 2A and FIG. 3C, represents the circumferential direction of the PET equipment 1 (and also the circumferential direction of the ring-like supporting members). The direction y illustrated in the same Figures represents the radial direction of the PET equipment 1 (and also the radial direction of the ring-like supporting members).

As illustrated in FIG. 2B, the detection module 20A overlaps with the ASIC substrate 20B in the end portion thereof to provide electrical connection thereon using the connector C1 and the connector C2 allocated in the overlapped portion. Both detection module 20A and ASIC substrate 20B overlapped in the end portion are mechanically connected each other using tightening screws or the like so that the detection module can easily be attached to and detached from the ASIC substrate.

Low-loss transmission of the gamma rays detection signals is ensured from the detection module 20A to the ASIC substrate 20B by employing connectors such as the connector C1 and the connector C2 providing a structure of electrical connection between the detection module 20A and the ASIC substrate 20B. In fact, the lower the loss, for instance, the better energy resolution can be obtained as the detection unit 21.

The detection module 20A is connected to the ASIC substrate 20B using tightening screws or the like so that the detection module can easily be attached to and detached from the ASIC substrate. Because of the mechanism employed therein, when a failure such as a detection trouble occurs in a detection unit 21 or ASIC 28, 29, what is necessary is to replace only the defective portion (the detection module 20A or ASIC substrate 20B). Furthermore, since the connector C1 such as the spring pin connector as described above is employed to provide electric connection between the detection module 20A and the ASIC substrate 20B, one of the substrate can easily be attached (or connected) to and detached (or disconnected) from the other substrate.

A shorter length (distance) of a circuit or a wiring is preferably used to transmit the gamma rays signal, because, in such a case, less noise will affect the signal in the circuit and wiring, and the detection signal will be less attenuated. When simultaneous measurement is processed in the PET equipment 1, it is preferable to use shorter length of a circuit and a wiring to minimize the time delay (as well as the degradation of the accuracy of the detecting time). Therefore, in this embodiment, the detector 21, condensers 21, analog ASICs 28 and digital ASIC 29 are sequentially arranged in this order on the unit substrate from the center axis to the outer in the radial direction of the PET equipment 1. This configuration employed therein makes it possible to minimize the length (distance) of the wiring that transmits a small gamma rays detection signal outputted from the detection unit 21 to an amplifier in the analog ASIC. With the configuration, the noise affecting the gamma rays detection signal can be reduced, and the gamma rays detection signal is less attenuated.

Alternatively, the condensers 26, resistors 27, and analog ASICs 28 provided on the ASIC substrate 20B can be arranged on the detection module 20A. In this case, the condensers 26, resistors 27, and analog ASICs 28 can be arranged closer to the ASIC substrate 20B rather than the detector unit 21. The distance (length of a wiring) between the detection unit 21 and the analog ASIC 28 can further be reduced because the detection module 20A includes the detection unit 21 and the analog ASIC 28.

Therefore, the influence of noises can further be reduced.

[Operations of the PET Equipment]

Operations of the Pet tomographic equipment having the configuration described above will be described below. Before start of radiographic examination, at first, a radioactive agent (including, for instance, 18F) for PET is previously administered to a subject H by injection or other method so that the radioactivity of the radioactive agent administered into a body of the subject H is, for instance, at around 370 MBq. The radioactive agent is selected according to an object of the examination (such as identification of a location of a cancer, examination of cardio arterial hemangioma, and the like). The administered radioactive agent gathers in an affected part of the subject H. In this state, the subject H is laid down on a bed.

An examiner who performs the PET examination (such as a medial radioactive ray engineer or a doctor) inputs required information depending on the examination object (such as a region from which tomographic images are to be obtained (an image region or a region of interest), the number of slices, a slicing space, an absorbed dose, and the like) via a data processor 2 (Refer to FIG. 1A). In this operation, a technique may be employed in which an information input screen not shown is displayed on the display unit 3 and the necessary data is inputted with a keyboard, a mouse, and the like. Then the bed 31 is removed in the longitudinal direction, and the subject H is inserted into a measurement space 32 until the examined region of the subject H (i.e., a position of a cancer) comes to a prespecified position. The operation of the PET equipment 1 is started.

A DC high voltage is applied to a section between an anode A and a cathode C in each detector 21 is loaded according to an instruction from the data processor 2, and the PET examination by the PET equipment 1 is started. The gamma rays generated by the radioactive agent and emitted from inside of a body of the subject H is detected by the detector 21. Namely, a pair of gamma rays are emitted in the directions opposite by about 180 degrees to each other when positrons emitted from the radioactive agent for PET extinguish, and the gamma rays are detected by the different detectors 21. The detector 21 outputs a signal indicating that the gamma rays were detected (gamma rays detection signal). This signal is inputted, via a signal line 24b, connectors C1, C2, and a capacitor 26, into a corresponding signal processing circuit (not shown) in the analog ASIC 28. This signal processing circuit amplifies the gamma rays detection signal and computes a pulse height value for the detected gamma rays. This pulse height value is converted to digital pulse height information by an analog/digital converter (ADC) not shown in the digital ASIC 29. The digital ASIC 29 furthermore outputs information concerning a position of the detector 21 having detected the gamma rays and time when the gamma rays were detected. The digital pulse height information, the information concerning a position of the detector 21 (positional information), and the information concerning the time when the gamma rays were detected (detected time information) are inputted into the data processor 2. A simultaneous counting device (not shown) in the data processor 2 counts, by using the detected time information, a pair of gamma rays generated in association with extinguishment of one positron as one count, and identifies positions of the two detectors 21 having detected the pair of gamma rays based on the positional information. Furthermore a tomographic information preparing device (not shown), which is an image information preparing device in the data processor 2, prepares, by using count values obtained in the simultaneous counting and the positional information for the detector 21, tomographic information (image information) of a region where the radioactive agent gathers, namely a position of a malignant cancer in the subject. This tomographic information is displayed on the display device 3.

Effects obtained in this embodiment are described below.

(1) With the detector 21 according to the present invention, by using the conductive adhesive agent 21A which is a rigid conductive adhesive noncompliant to thermal stress (with the Young's modulus in the range from 350 Mpa to 1000 MPa), it is possible to improve electric conductivity of a metallic filler contained in the conductive adhesive agent 21A and also to prevent distortion of a signal passing therethrough. In addition, by using a material with the linear expansion coefficient in the range from $5 \times 10^{-6}/°$ C. to $7 \times 10^{-6}/°$ C. which is close to that of the detecting element 211 made of CdTe as a main material for the detector 21, it is possible to make small the possibility of generation of thermal stress in the detecting element 211 made of CdTe as well as in the conductive members 22, 23. Because of the feature, it is possible to obtain the detector 21 in which distortion of a signal outputted from the detecting element 211 hardly occurs, and also which has the improved sensitivity for gamma ray detection and improved energy resolution and time precision.

(2) Since thermal stress can be suppressed to a sufficiently low level, even when the detecting elements 211 and the conductive members 22, 23 are laminated on each other, deterioration of the characteristics is rather small.

(3) Since thermal stress can be suppressed to a sufficiently low level, the detecting element 211 can be formed with a smaller thickness well suited for lamination, and at the same time the performance and sensitivity of the detector 21 can be improved. In the PET equipment 1, it is necessary to efficiently capture gamma rays at 511 KeV, and to satisfy this requirement, the detecting element 211 must be thick. When the detecting element 211 is thick, however, migration distance of electrons or holes become longer. Therefore, the energy resolution and prevision in recognition of the incoming time disadvantageously become lower. If a plurality of detecting elements 211 each having a small thickness can be laminated, since the migration distance of electrons or holes can be shortened, the energy resolution and prevision in recognition of the incoming time are improved. Furthermore a volume occupancy ratio of by the detecting 211 can be made larger and also a volume of the detector can advantageously be increased, and therefore the performance of the PET equipment 1 can be improved.

(4) An iron-nickel alloy or the like is used as a material for the conductive members 22, 23, and therefore signal acquisition can be performed in the stable condition, and also the detector 21 which is rigid when mounted can be obtained.

(5) In the detector 21, cathodes C or anodes A of the adjoining detecting elements 211 are provided at positions opposite to each other, and thereby the cathodes or the anodes can share the conductive members 22, 23. In addition, because of the laminated structure enabling suppression of thermal stress to a sufficiently low level, the detecting elements 22, 23 are excellent in adhesion as well as in conductivity. Therefore, a bias voltage for collecting an electric charge can be loaded to a section between the cathode C and the anode A in the stable condition. Furthermore, it is not necessary to provide an electric insulator between the detecting elements 211, and the detecting elements 211 can be provided at positions close to each other. Thus, sensitivity is improved and time it takes for examination is reduced.

(6) Since the conductive members 22, 23 have protruding sections 22a, 23a extended downwardly toward the wiring board 24, and the protruding sections 22a, 23a are attached to the wiring board 24, the conductive members 22, 23 can easily be mounted onto the wiring board 24. Furthermore, since the protruding sections 22a, 23a extend downwardly toward the wiring board 24 and do not protrude sideward from the detector 21, the detectors 21 can be provided at positions close to each other.

(7) Since the conductive members 22, 23 are larger than the anode A and the cathode C which function as side faces of the detecting element 211, the conductive members 22, 23 can advantageously protect the fragile detecting element 211, and when the detector 21 is attached to the wiring board 24, it is possible to advantageously prevent the detecting element 211 from sliding on and giving damage to a surface of the writing board 24. Namely the conductive members 22, 23 functions as protection members for the detecting element 211.

(8) Since the protruding sections 22a, 23a extend down at positions spaced from each other on the bottom surface which is one side face of the detector 21, the electric insulating performance can be improved.

(9) Since the protruding sections 22a, 22b are provided so that the plate-like faces thereof are parallel to the direction Y, the gamma rays are less scattered by the protruding sections 22a, 23a. Further a quantity of heats delivered from the wiring board 24 via the protruding sections 22a, 23a to the detector 21 can be reduced, which is advantageous for stabilizing performance of the detector 21.

(10) In the PET equipment 1 using the detectors 21 therein, a device as an ASIC incorporating a number of amplifying circuits associated with the detectors 21 respectively is used to form a signal processing circuit. Therefore, each of the detectors 21 can be down-sized, and also increase in the number of detectors can be accommodated. As a result, the space resolution can further be improved.

(11) Since it is possible to configure the detection module 20A on which a number of the detectors 21 having the high energy resolution can be mounted, a highly quantitative inspection can be performed in the three-dimensional image pick-up operations.

(12) By covering the detector 21 provided on the wiring board 24 with an electrically insulating material, dielectric breakdown in the detector 21 can be prevented.

Embodiment 2

Figure 9:
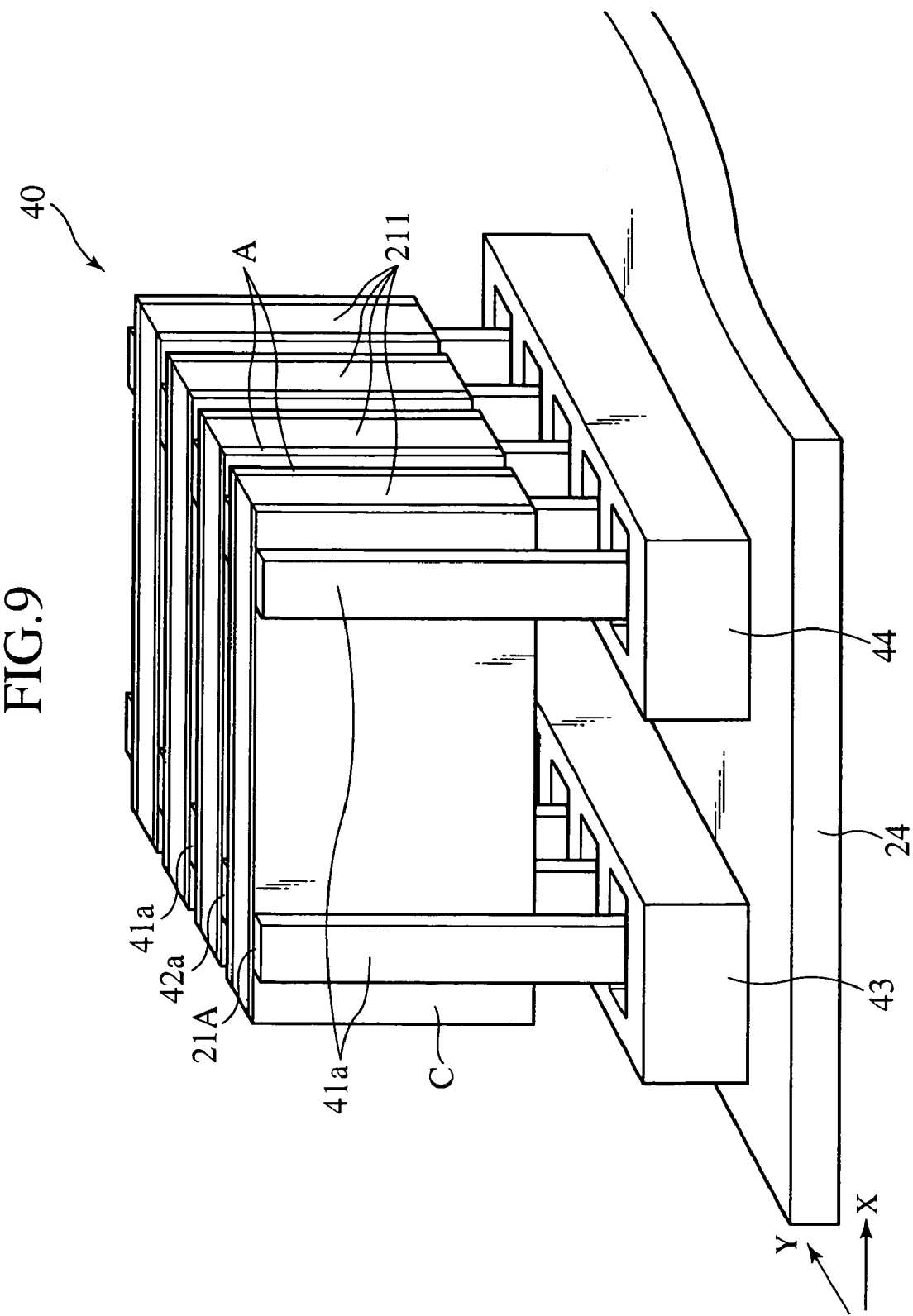
FIG. 9 is a perspective view illustrating a detector which can be used in the PET equipment according to another embodiment of the present invention.

The detector used in the PET equipment according to another embodiment of the present invention is described below. The detector according to this embodiment can be used in place of the detector 21 which is used in the PET equipment 1 shown in FIG. 1, and as shown in FIG. 9, a detector 40 has conductive members 41a, 42a each having a form like an elongated plate. An incoming direction of a radioactive ray is X axis direction. Portions of the PET equipment according to an embodiment 2 other than the detector 40 are the same as those of the PET equipment according to the first embodiment described above and shown in FIG. 1.

The conductive members 41a, 42a each has an elongated plate-like form and can be inserted into sockets 43, 44 provided on the wiring board 24, and are connected to terminals not shown and formed in the sockets 43, 44. Also in this detector 40, the conductive members 41a, 42a are provided between the same types of electrodes facing against each other and are attached to the electrodes with the conductive adhesive agent 21A, and the conductive member 41a is attached to the cathodes C provided at two ends of the detector 40 with the conductive adhesive agent 21A. The conductive members 41a, 42a are detachably provided in the sockets 43, 44, and the conductive member 41a is connected to the cathode C of the detecting element 211, while the conductive member 42a is connected to the anode A of the detecting element 211.

In this embodiment, the effects (1) to (6) and (10) to (12) achieved in the embodiment 1 can be obtained. This embodiment additionally provides the following effects.

(13) In this embodiment, since the conductive members 41a, 42a each have an elongated plate-like form allowing for insertion into the sockets 43, 44 respectively, the areas thereof are smaller as compared to those of the conductive members 22, 23 in the embodiment 1, which enables reduction of loss of gamma rays. As the areas of the conductive members 41a, 42a are smaller, influence by the thermal stress becomes a little smaller, but when adhered with the conductive adhesive agent 21A, a detection signal outputted from the detecting element 211 hardly distorts with the gamma ray detection sensitivity improved. Thus, the detector 40 having the improved energy resolution and improved time precision can be obtained.

Embodiment 3

Figure 10:
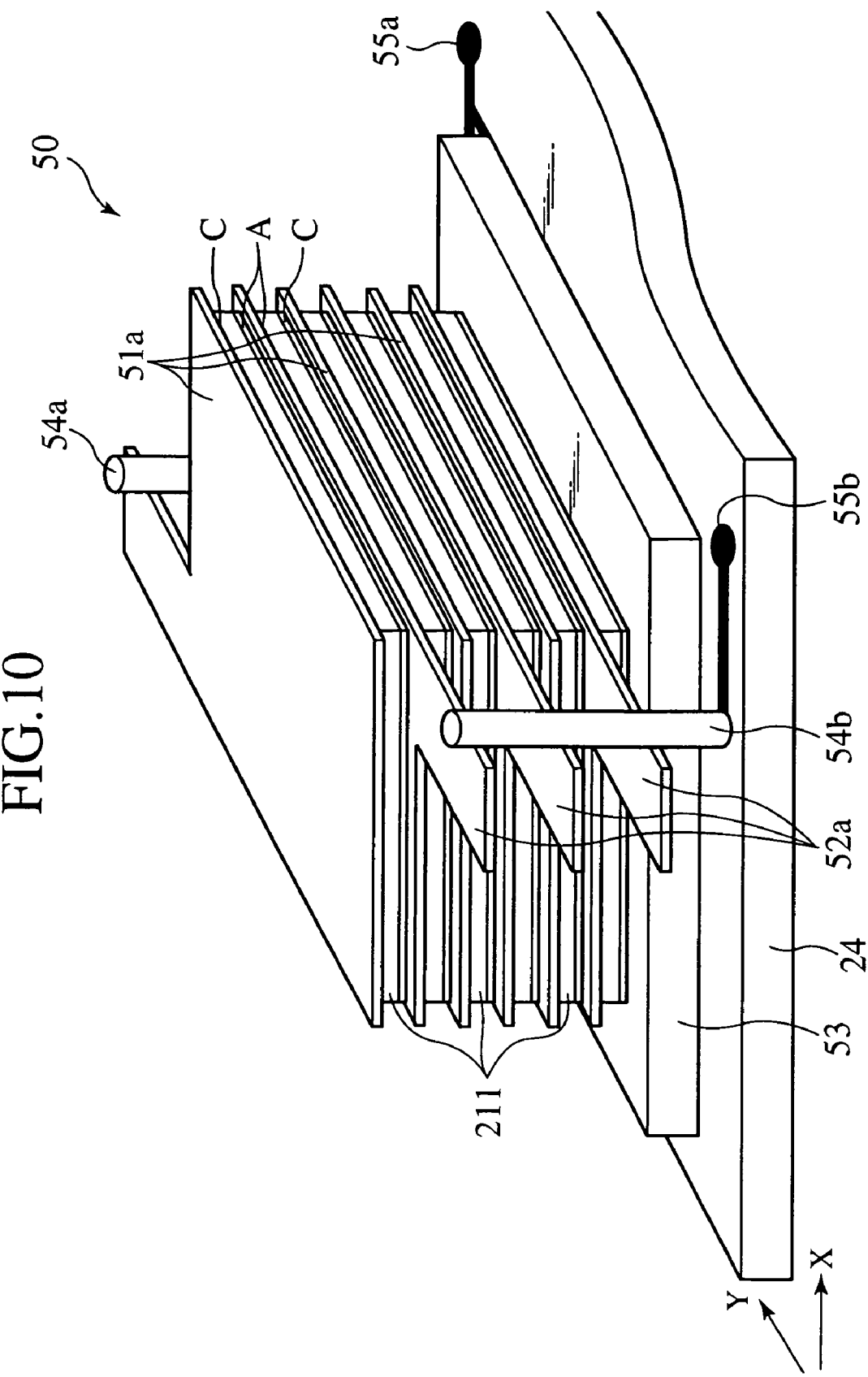
FIG. 10 is a perspective view illustrating a detector which can be used in the PET equipment according to still another embodiment of the present invention.

A detector adapted to use in the PET equipment according to a third embodiment of the present invention is described below. The detector according to this embodiment can be used in places of the detector 21 shown in FIG. 1 which is used in the PET equipment 1, and has the detecting elements 211 and the conductive members 51a, 52a horizontally laminated alternately on the wiring board 24 as shown in FIG. 10. An incoming direction of a radioactive ray is X axis direction. Portions of the PET equipment according to this embodiment other than a detector 50 are the same as those of the PET equipment according to the embodiment 1 shown in FIG. 1.

The detector 50 is adhered to an electrode base 53 mounted and attached to a surface of the wiring board 24 with a conductive adhesive agent (not shown like in the first embodiment). The electrode base 53 is made of an iron-nickel alloy, and for instance, the 42% alloy (with the Fe content of 58% and Ni content of 42%) can be used for this purpose. A conductive member 51*a* is a cathode C to which a bias voltage is applied, and is connected to a circuit 55*a* on the wiring board 24 with the bus bar 54*a*. A conductive member 52*a* is connected to a circuit 55*b* on the wiring board 24 with a bus bar 54*b*.

In this embodiment, the effects (1) to (5), (7), and (10) to (12) can be obtained. This embodiment furthermore provides the following effect.

(14) In the detector 50, the detecting element 211 and the conductive members 51*a*, 52*a* are horizontally laminated and attached to the wiring board 24, which advantageously stabilizes the mounting state. In addition, since the detector 50 is provided on the electrode base 53 made of the 42% alloy, and the cathode C is contacted to the detector 50, the production cost is cheaper as compared to that in the case where a material such as alumina is used for the same purpose. Furthermore, the electrode 53 is made of the 42% alloy, and therefore, unlike the electrode made of, for instance, alumina, such troubles as breakage never occurs, and maintenance works such as exchange of the detector 50 with a new one can be performed more easily.

Embodiment 4

In the embodiment 1, the semiconductor detector elements and the metallic conductive members have similar linear expansion coefficients. The semiconductor detector elements are made of cadmium telluride as a main material having the linear expansion coefficient about $6 \times 10^{-6}/°$ C., and metallic conductive members are made from a material having the linear expansion coefficient in the range from $5 \times 10^{-6}/°$ C. to $7 \times 10^{-6}/°$ C.

This feature is adaptable for other materials. For example, the ratio of their linear expansion coefficients is preferably in the range of 0.83 to 1.17. This range is calculated from those linear expansion coefficients described above.

Figures 11, 12:
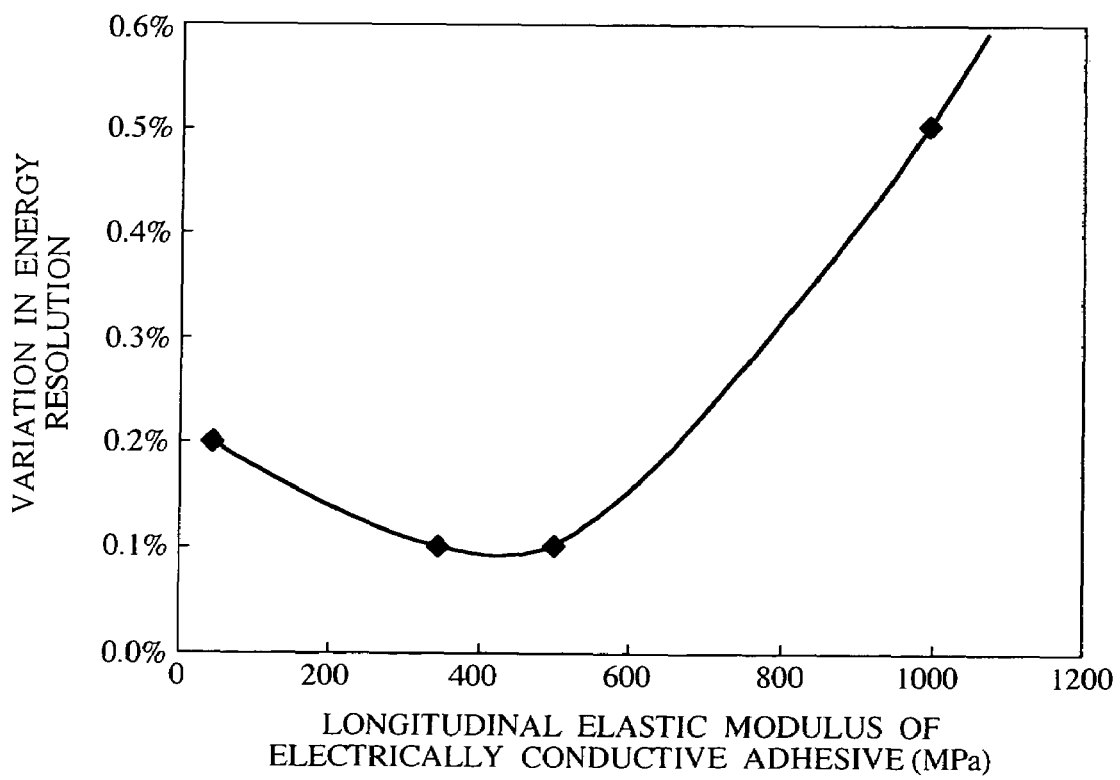
FIG. 11 is a table indicating a relation between a longitudinal elastic modulus (the Young's modulus) of a conductive adhesive and an energy resolution based on experimental data.
FIG. 12 is a graph indicating a relation between variations in energy resolution and the longitudinal elastic modulus (the Young's modulus) of the conductive adhesive.

Reference FIG. 11 is a table indicating a relation between a longitudinal elastic modulus (the Young's modulus) of a conductive adhesive and an energy resolution based on experimental data. Reference FIG. 12 is a graph indicating a relation between variations in energy resolution and the longitudinal elastic modulus (the Young's modulus) of the conductive adhesive. In these figures, a material whose linear expansion coefficient ranges from $5 \times 10^{-6}/°$ C. to $7 \times 10^{-6}/°$ C. was used as the conductive member. In addition, a value obtained by subtracting the minimum value of the energy resolution from the maximum value of the energy resolution was applied as variations in energy resolution.

In turn, it is necessary that a level at which energy resolution or time precision of the semiconductor radioactive ray detector is satisfactory should be so set that variations in energy resolution is 0.1% or less. Specifying a range with which 0.1% or less is satisfied from Reference FIG. 12 shows that values ranging 350 MPa to 500 MPa correspond to 0.1% or less. In this case, since a gradient is large in a longitudinal elastic modulus (the Young's modulus) value smaller than 350 MPa, FIG. 12 indicates that variations in energy resolution tend to remarkably exceed 0.1%. Also in the case of a longitudinal elastic modulus (the Young's modulus) value larger than 500 MPa, its gradient is steep. Therefore, it indicates a tendency that variations in energy resolution remarkably exceed 0.1%.

Figure 13:
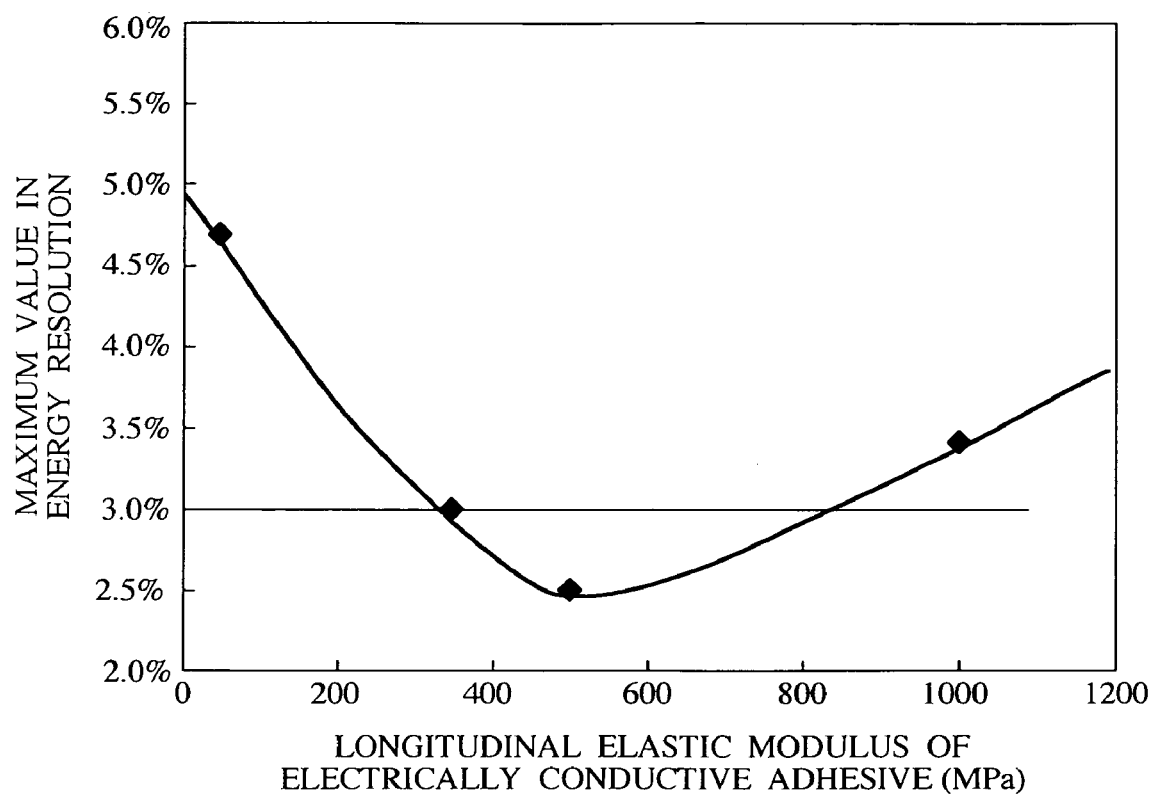
FIG. 13 is a graph indicating a relation between the maximum value of the energy resolution and the longitudinal elastic modulus (the Young's modulus) of the conductive adhesive.

Reference FIG. 13 is a graph indicating a relation between the maximum value of the energy resolution and the longitudinal elastic modulus (the Young's modulus) of the conductive adhesive. The energy resolution marked at 3.0% indicates that the product is slightly below the certain level but obtains the desirable properties. When the Young's modulus of the conductive adhesive agent is in the range from 350 MPa to 850 MPa, the energy resolution marked below 3.0%.

In the embodiment 1, connection members CP, AP for the wiring board 24 are provided for the conductive members 22, 23 respectively. However, the configuration is allowable in which the connection member CP is provided on the wiring board 24 and used as a common electrode, and the conductive member 22 is connected to the connection member CO with an adhesive agent or the like. In the first embodiment, the protruding section 23*a* of the conductive member 23 connected to the anode A is connected to the connection member AP and the protruding section 22*a* of the conductive member 22 connected to the cathode C is connected to the connection member CP. However, the configuration is allowable in which the protruding section 23*a* is connected to the connection member CP and the protruding section 22*a* is connected to the connection member AP. In this case, the cathode C functions as an electrode which outputs a gamma rays detection signal, while the anode A functions as an electrode to which a bias voltage is applied. Any pattern can be realized so long as a voltage applied to the anode A and that to the cathode C are reverse to each other.

In the first and second embodiments, an electric potential at the cathode A is set to the level substantially equal to the ground potential, and an electric potential at the cathode C to −500 V. However, there is not specific restriction over the electric potentials so long as the potentials are reverse to each other, and the voltage values may be set in a range allowing for normal functions of the PET equipment. Also the configuration is allowable in which the cathode C is used as an electrode from which a radioactive ray detection signal is acquired and the anode A as an electrode to which a bias voltage is applied.

Although embodiments of the present invention have been described above with reference to PET equipment (Refer to FIG. 1) as a nuclear medicine diagnosis apparatus, the detector and the detection module of the present invention can be applied not only to the PET equipment 1, but also to single photo emission computer tomography (SPECT) equipment as well as to a gamma ray camera. The PET equipment and the SPECT equipment are common in the point that a subject is photographed with a three-dimensional image forming function. Since the SPECT equipment is based on the measurement principle that a single photon is emitted for detection, the equipment cannot be used for simultaneous measurement, and to overcome this defect, a collimator is used for adjusting an incoming position (angle) of the gamma rays. On the other hand, the gamma ray camera provides a two-dimensional image, and has a collimator for adjusting an incoming angle of the gamma rays.

It is possible to apply the present invention to a nuclear medicine diagnosis apparatus based on a combination of the PET equipment or the SPECT equipment according to the present invention with an X-ray CT. While specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the above description has been made in an illustrative fashion, and not a restrictive one. Accordingly, the scope of the invention should properly be determined with reference to the appended claims, along with the full range of equivalents to which such claims are entitled.

What is claimed is:

1. A semiconductor radioactive ray detector using cadmium telluride as a main material and having a structure with plate-like elements made of cadmium telluride and metallic conductive members laminated alternately, said plate-like elements made from cadmium telluride and said metallic conductive members being adhered to each other with a conductive adhesive agent,
wherein said conductive adhesive agent has a Young's modulus in the range from 350 MPa to 1000 MPa and said metallic conductive members are made from a material having the linear expansion coefficient in the range from $5 \times 10^{-6}/°$ C. to $7 \times 10^{-6}/°$ C.

2. The semiconductor radioactive ray detector according to claim 1, wherein some of a plurality of said conductive members are provided between the same type of electrodes facing each other and attached to the electrodes, and remaining ones of the conductive members are attached to electrodes positioned at two ends of said semiconductor radioactive ray detector.

3. The semiconductor radioactive ray detector according to claim 1,
wherein said conductive member has a size sufficient to cover a corresponding electrode surface of said plate-like element.

4. The semiconductor radioactive ray detector according to claim 3, wherein said conductive member is larger than a corresponding electrode surface of the plate-like element.

5. A radioactive detection module comprising the semiconductor radioactive ray detector according to claim 1 and a wiring board with the semiconductor radioactive ray detector attached thereto,
wherein a connecting member with the conductive member attached thereto is provided on a surface of said wiring board, and said connecting member is provided on said wiring board as a common connecting member for a plurality of said semiconductor radioactive ray detectors.

6. The radioactive detection module according to claim 5, wherein said plate-like element made of cadmium telluride and said metallic conductive member are attached in a direction perpendicular to a surface of said wiring board.

7. The radioactive detection module according to claim 6, wherein said metallic conductive member is inserted into and connected to a connector provided on said wiring board.

8. The radioactive detection module according to claim 5, wherein said plate-like element made of cadmium telluride and said metallic conductive member are attached are attached in a direction parallel to a surface of said wiring board.

9. A nuclear medicine diagnosis apparatus comprising:
the radioactive ray detection module according to claim 5; and
an image information forming device for forming an image by using information acquired based on a radioactive detection signal outputted from said semiconductor radioactive ray detector.

10. The nuclear medicine diagnosis apparatus according to claim 9 further comprising:
an integrated circuit including a plurality of signal processors for processing radioactive ray detection signals outputted from said plurality of semiconductor radioactive ray detectors, said circuit attached to said wiring board.

11. A semiconductor radioactive ray detector using cadmium telluride as a main material and having a structure with plate-like elements made of cadmium telluride and metallic conductive members laminated alternately, said plate-like elements made from cadmium telluride and said metallic conductive members being adhered to each other with a conductive adhesive agent,
wherein said conductive adhesive agent has a Young's modulus in the range from 350 MPa to 1000 MPa and a material for said metallic conductive member is at least one selected from the group consisting of iron-nickel alloy, iron-nickel-cobalt alloy, chromium, and tantalum.

12. A semiconductor radioactive ray detector using cadmium telluride as a main material and having a structure with plate-like elements made of cadmium telluride and metallic conductive members laminated alternately, said plate-like elements made from cadmium telluride and said metallic conductive members being adhered to each other with a conductive adhesive agent,
wherein said conductive adhesive agent is rigid and is selected to have a Young's modulus in the range of 350 MPa to 500 MPa, after hardening at room temperature.

13. The semiconductor radioactive ray detector according to claim 12, wherein said conductive adhesive agent is selected to have a Young's modulus of approximately 500 MPa.

14. The semiconductor radioactive ray detector according to claim 12, wherein a material for said metallic conductive members is at least one selected from the group consisting of iron-nickel alloy, iron-nickel-cobalt alloy, chromium, and tantalum.

15. The semiconductor radioactive ray detector according to claim 12, wherein the difference of energy resolution is below 0.1% in the range of linear expansion coefficient of said metallic conductive members between $5 \times 10^{-6}/°$ C. to $7 \times 10^{-6}/°$ C.

16. A semiconductor radioactive ray detector having a structure with plate-like elements made of semiconductor and metallic conductive members laminated alternately, said plate-like elements and said metallic conductive members being adhered to each other with a conductive adhesive agent,
wherein said plate-like elements and said metallic conductive members have similar linear expansion coefficients, and said conductive adhesive agent is rigid and is selected to have a Young's modulus in the range of 350 MPa to 1000 MPa, after hardening at room temperature.

17. The semiconductor radioactive ray detector according to claim 16, wherein a ratio of linear expansion coefficients of said plate-like elements and said metallic conductive members is in a range of 0.83 to 1.17.

18. The semiconductor radioactive ray detector according to claim 16, wherein said conductive adhesive agent has a Young's modulus in the range of 350 MPa to 850 MPa.

19. A nuclear medicine diagnosis apparatus comprising:
a bed,
semiconductor radioactive ray detectors having a structure with plate-like elements made of semiconductor and metallic conductive members laminated alternately, said plate-like elements and said metallic conductive elements being adhered to each other with a conductive adhesive agent,
wherein said plate-like elements and said metallic conductive members have similar linear expansion coefficients, and said conductive adhesive agent is rigid and is selected to have a Young's modulus in the range of 350 MPa to 1000 MPa, after hardening at room temperature; and
an image forming device which forms an image by using information acquired based on a radioactive detection signal outputted from said semiconductor radioactive ray detectors.

20. In a PET having a bed, semiconductor radioactive ray detectors, and a data processor, at least one of said semiconductor radioactive ray detectors comprising:
 plate-like elements made of a semiconductor, and metallic conductive members
  wherein said plate-like elements and metallic conductive members are laminated alternately, are adhered to each other with a conductive adhesive agent, and have similar linear expansion coefficients,
  wherein said conductive adhesive agent, which is rigid and is selected to have a Young's modulus in the range of 350 MPa to 1000 MPa, after hardening at room temperature.

* * * * *